United States Patent [19]

Batz et al.

[11] 4,133,949

[45] Jan. 9, 1979

[54] DICARBOXYLIC ACID ESTERS OF CARDIAC GLYCOSIDES

[75] Inventors: Hans-Georg Batz, Tutzing; Hans-Ralf Linke, Wielenbach; Klaus Stellner, Bernried; Günter Weimann, Tutzing, all of Germany

[73] Assignee: Boehringer Mannheim GmbH, Mannheim-Waldhof, Germany

[21] Appl. No.: 715,020

[22] Filed: Aug. 16, 1976

[30] Foreign Application Priority Data

Aug. 20, 1975 [DE] Fed. Rep. of Germany ....... 2537129

[51] Int. Cl.² .............................................. C07J 19/00
[52] U.S. Cl. .............................. 536/7; 260/112.5 R; 260/121; 424/1; 424/12; 424/182; 536/5
[58] Field of Search ................................ 536/4, 5, 6, 7

[56] References Cited

U.S. PATENT DOCUMENTS 3,963,697 6/1976 Coombes .................................. 536/7

Primary Examiner—Johnnie R. Brown

Attorney, Agent, or Firm—Burgess, Dinklage & Sprung

[57] ABSTRACT

New reactive asymmetrical dicarboxylic acid ester compounds of the formula

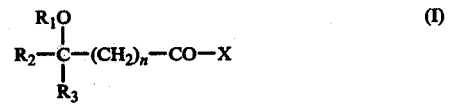

wherein $R_1$ is an alkyl radical containing up to 3 carbon atoms or is a digoxin or digitoxin residue, $R_2$ and $R_3$, which may be the same or different, are alkoxy radicals containing up to 3 carbon atoms or together represent an oxygen atom, X is a cyanomethoxy, succinimide-N-oxy, N-methyl-pyridiniumoxy, 2,4-dinitrophenoxy, 2,4,5-trichlorophenoxy, pentachlorophenoxy, phenylthio, p-nitrophenoxy, p-nitrophenylthio, piperidyl-N-oxy, phthalimido-N-oxy or benztriazol-N-oxy radical and n is 2, 3, 4 or 5. are useful for the preparation of reagents for the investigation of cardiac glycosides (Digitalis glycosides).

4 Claims, No Drawings

DICARBOXYLIC ACID ESTERS OF CARDIAC GLYCOSIDES

The present invention is concerned with novel reactive asymmetrical dicarboxylic acid ester compounds useful for the preparation of reagents for the investigation of cardiac glycosides (Digitalis glycosides). The invention also relates to processes for the preparation of such compounds and to compositions and methods for the investigation of cardiac glycosides.

The methods used for the investigation of Digitalis glycosides and especially for the measurement of the pharmacological level of such glycosides are immunological tests in aqueous or physiological solution, for example, in plasma, serum and urine. Such immune tests for the determination of digitoxin and digoxin are known. Thus, according to the process described by G. C. Oliver, B. M. Parker, D. L. Brasfield and C. W. Parker in "The Measurement of Digitoxin in Human Serum by Radioimmunoassay" (J. Clin. Investig., 47, 1035/1968), a certain amount of an anti-digitoxin serum prepared by means of immunological standard processes is reacted with an aqueous or physiological solution, the digitoxin content of which is to be determined, for example with test plasma, serum or urine, or with a standard digitoxin solution, in each case together with a constant amount of digitoxigenin which is either radioactively marked or is bound on to an enzyme and, in each case in such a manner that the antigenic properties remain unchanged. After incubation of the mixture, the digitoxin or digitoxigenin bound with the antibody is separated from free digitoxin or digitoxigenin and the radioactivity or the enzyme activity is measured. The reagent, i.e., the radioactive-marked or enzyme-bound digitoxin, is a 3-0- succinyl-digitoxigenin (prepared by reacting digitoxigenin with succinic acid anhydride) condensed with a peptide, an amino acid or an amino acid ester.

German Patent No. 2,142,422 describes an analogous process for the determination of digoxin, which is also based upon an immune test, in which the reagent used is also prepared from digoxigenin (i.e., 12- hydroxydigitoxigenin) by succinylation, the hydroxyl group in the 12-position being protected, followed by condensation with a peptide, an amino acid or an amino acid ester. It is also known to bind the succinylated genin, for the anti-body preparation as antigen, on to a protein, for example on to bovine serum albumin (BSA).

Since the complex of the antibody with the genin is less stable than the corresponding complex with the complete cardiac glycoside, it has also been suggested to condense the cardiac glycoside, via the terminal sugar residue, with an amino acid or a protein. Thus, V. P. Butler and J. P. Chen (Proc. Nat. Acad. Sci. U.S., 57, 71/1966) have described the oxidation of the terminal digitoxose residue by means of periodate, followed by condensation with a protein, such as BSA, to give an immunogen. The same process is described in German Patent No. 2,331,922 but for the preparation of iodisable digoxinamino acid and -peptide derivatives.

Since digoxin is extraordinarily sensitive towards acids and lyes, the digoxin-amino acid derivative is, under the drastic conditions of the last-mentioned process, only obtained in a yield of 10% of theory. The same disadvantage of a low yield also occurs in the case of the reaction with a protein but with the added disadvantage that purification of the digoxin-protein derivative is no longer possible as in the case of a low molecular weight amino acid derivative so that immunogens obtained in this way also contain by-products, for example isomerised digoxin. A further disadvantage of this known process for the preparation of a digoxin reagent is the irreversible change of the terminal sugar residue in the digoxin molecule, as well as its direct linking with the protein or the amino acid. In this way, the steric relationships within the digoxin molecule are changed, which, in turn, influences the exactitude of the test carried out with this molecule as reagent in which ultimately the antibody complex of this molecule is compared with the antibody complex of the free digoxin.

It is an object of the present invention to avoid these disadvantages and to provide compounds which enable Digitalis glycosides, for example digoxin or digitoxin, to be condensed, without changing their molecular structure, via a "bridge" with compounds containing at least one amino group, for example amines, amino acid derivatives or proteins, to give compounds which can be used for the preparation of reagents for the investigation of cardiac glycosides.

Thus, according to the present invention, there are provided reactive asymmetrical dicarboxylic acid esters of the general formula:

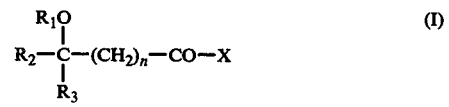

wherein $R_1$ is an alkyl radical containing up to 3 carbon atoms or is a digoxin or digitoxin residue, $R_2$ and $R_3$, which may be the same or different, are alkoxy radicals containing up to 3 carbon atoms or together represent an oxygen atom, X is a cyanomethoxy, succinimide-N-oxy, N- methyl-pyridiniumoxy, 2,4-dinitrophenoxy, 2,4,5-trichlorophenoxy, pentachlorophenoxy, phenylthio, p-nitrophenoxy, p-nitrophenylthio, piperidyl-N-oxy, phthalimido-N-oxy or benztriazol-N-oxy radical and n is 2, 3, 4 or 5.

A preferred group of esters according to the present invention are those in which $R_1$ is a methyl radical, $R_2$ and $R_3$ are both methoxy radicals, X is a cyanomethoxy, succinimido-N-oxy, 2,4,5-trichlorophenoxy or benztriazol-N-oxy radical and n is 2 or 3 and another preferred group of esters according to the present invention are those in which $R_1$ is a digoxin or digitoxin residue, $R_2$ and $R_3$ together represent an oxygen atom, X is a cyanomethoxy, succinimido-N-oxy, 2,4,5-trichlorophenoxy or benztriazol-N-oxy radical and n is 2 or 3.

The present invention also provides a process for the preparation of the dicarboxylic acid esters (I), wherein a mono-ortho-trimethyl, -triethyl or -tripropyl ester of a dicarboxylic acid containing 4 to 7 carbon atoms is reacted, in the form of an alkali metal salt, in the presence of a crown ether or kryptate, in a polar or nonpolar aprotic organic solvent with a reactive compound containing the residue X, for example with chloroacetonitrile, a hydroxysuccinimide-sulphonate, N-hydroxybenztriazole tosylate or trifluoromethylsulphonate or 2,4,5-trichlorophenyl-sulphonate, and, if desired, is subsequently reacted with digoxin or digitoxin in the presence of p-toluene-sulphonic acid.

Examples of reactive dicarboxylic acids of the above-given general formula (I) include the following: glutaric acid ω-orthotrimethyl ester-ω'-hydroxysuccinimide ester, glutaric acid ω-orthotrimethyl ester-ω'-cyanomethyl ester, succinic acid ω-orthotriethyl ester-ω'-cyanomethyl ester, adipic acid ω-orthotripropyl ester-ω'-hydroxysuccinimide ester, succinic acid ω-methyl ester-ω'-cyanomethyl ester, glutaric acid ω-propyl ester-ω'-cyanomethyl ester, adipic acid ω-ethyl ester-ω'-hydroxysuccinimide ester, digoxin-4'''-succinylcyanomethyl ester, digoxin-4'''-glutarylcyanomethyl ester, digoxin-4'''-glutaryl- hydroxysuccinimide ester, digitoxin-4'''-adipinyl-hydroxysuccinimide ester, succinic acid- ω-methyl ester-ω'-2,4,5-trichlorophenyl ester, succinic acid ω-orthotriethyl ester-ω' -hydroxybenztriazol ester, digoxin-4'''-succinyl-2,4,5-trichlorophenyl ester, digitoxin-4'''-succinyl-2,4,5-trichlorophenyl ester, glutaric acid ω-orthotrimethyl ester-ω'-2,4,5-trichlorophenyl ester, glutaric acid ω-propyl ester-ω'-hydroxybenztriazol ester, digoxin-4'''-glutaryl-2,4,5-trichlorophenyl ester, digitoxin-4'''-glutaryl-hydroxybenztriazol ester, adipic acid ω-orthotriethyl ester-ω'-2,4,5-trichlorophenyl ester, adipic acid ω-methyl ester-ω'-hydroxybenztriazol ester, pimelic acid ω-orthotrimethyl ester-ω'-hydroxysuccinimide ester, pimelic acid ω-orthotrimethyl ester-ω'-cyanomethyl ester pimelic acid ω-orthotriethyl ester-ω'-2,4,5-trichlorophenyl ester, pimelic acid ω-orthotrimethyl ester-ω'-hydroxybenztriazol-ester, pimelic acid ω- orthotripropyl ester-ω'-cyanomethyl ester, pimelic acid ω-methyl ester-ω'-2,4,5-trichlorophenyl ester, digoxin-4'''-pimelinylcyanomethyl ester, digoxin-4'''-pimelinyl-hydroxysuccinimide ester, digoxin-4'''-pimelinyl-2,4,5-trichlorophenyl ester, digoxin-4'''-pimelinyl-benztriazol-N-yl ester, pimelic acid ω-digitoxin-4'''-yl-ω-orthodiethyl ester-ω'-2,4,5-trichlorophenyl ester.

The reactive dicarboxylic acids according to the present invention are outstandingly useful for the preparation of reagents for the investigation of Digitalis glycosides by means of immunological tests of the initially mentioned type. These carboxylic acid esters can be reacted with a radioactive-marked compound containing at least one amino group, for example with an amino group-containing compound which can be iodised with $^{125}I$, such as tyramine, histidine, tyrosine or tyrosine ethyl ester or a peptide containing tyrosine, a tracer being obtained, or can be reacted with a biologically active protein for the preparation of antibodies, for example with bovine serum albumin, and the compounds according to the present invention can subsequently also be condensed with an enzymatically-active protein to give a reagent for the ELISA test. Thus, the present invention provides compounds which can be used for the preparation of reagents which are similar in their chemical structure but with which reagents it is possible to measure completely different values, namely, antibody activity, enzyme activity and radioactivity.

A further advantage of the compounds according to the present invention is that the hydrophilic properties thereof can be adapted to the particular purpose of use by the choice of the ω'-ester, i.e., by the choice between dicarboxylic acid esters of general formula (I), in which X is a cyanomethyl, succinimido-N-oxy, N-methylpyridiniumoxy 2,4-dinitrophenoxy, 2,4,5-trichlorophenoxy, pentachlorophenoxy, phenylthio, p-nitrophenoxy, p-nitrophenylthio, piperidyl-N-oxy, phthalimido-N-oxy or benztriazol-N-oxy radical, the cyanomethyl ester derivatives usually being more hydrophilic than the corresponding hydroxysuccinimide ester derivatives.

A further advantage of the compounds according to the present invention is that they can be fixed on to carrier substances, for example on to molecular sieves but also on to polystyrene, and can be used for affinity chromatography, especially on hydrophilic, amino group-containing gels, molecular sieves or the like. These gelbound substances serve as immune adsorbents and can thus be used for the purification of antibodies.

When carrying out the preparation of the reactive dicarboxylic acid esters according to the present invention, the polar or non-polar aprotic organic solvent used is preferably benzene or chloroform. Furthermore, the hydroxysuccinimide-sulphonate used is preferably the methyl-sulphonate or p-toluene-sulphonate employed as hydroxysuccinimide.

The starting material for the preparation of the new reactive dicarboxylic esters (I) is a mono-orthotrimethyl, -triethyl or -tripropyl ester of a dicarboxylic acid containing 4 to 6 carbon atoms in the form of an alkali metal salt, for example glutaric acid monoorthotrimethyl ester.

Glutaric acid monoorthotrimethyl ester can be prepared by passing 10.7 g. hydrogen chloride, with ice cooling, into a mixture of 37.3 g. ethyl cyanobutyrate and 12 ml. anhydrous methanol. After standing for 5 days in a refrigerator, glutaric acid ω-imido-O-methyl ester-ω'-ethyl ester hydrochloride slowly crystallises out. It is digested four times with anhydrous diethyl ether, filtered off with suction, with the exclusion of air, and dried over potassium hydroxide. Excess methanol is added to the imido ester salt thus obtained, with the exclusion of air and moisture. A first, the crystals go into solution and then, after standing for 12 hours at ambient temperature, precipitation of ammonium chloride slowly commences. The reaction mixture is left to stand for a further 48 hours and then precipitation is completed by the addition of a threefold amount of diethyl ether. The precipitate is then filtered off, the filtrate is evaporated and the residue is taken up in anhydrous diethyl ether, again filtered and the filtrate again evaporated. The glutaric acid ω-orthotrimethyl ester-ω'-ethyl ester remaining behind is subsequently distilled (b.p. 55–60° C./0.05 mm.Hg.). The yield over these first two steps is 41% of theory.

The same compound, i.e., glutaric acid ω-orthotrimethyl ester-ω'-ethyl ester, is obtained but in smaller yield when excess methanol is added to glutaric acid ω-imido-O-methyl ester-ω'-ethyl ester tetrafluoroborate, which can be prepared from glutaric acid ethyl ester amide by reaction with trimethyloxonium tetrafluoroborate.

The glutaric acid ω-orthotrimethyl ester- ω'-ethyl ester is dissolved in 50 ml. acetone and mixed with the equivalent amount of potassium hydroxide in 10 ml. water and stirred for 3 hours at ambient temperature. The acetone and the bulk of the water is then stripped off and the residue is mixed with anhydrous methanol. Upon evaporation, the potassium salt of the glutaric acid monoorthotrimethyl ester precipitates out and is filtered off and dried in a high vacuum. It can be used as starting material for the preparation of the reactive dicarboxylic acid esters according to the present invention.

The following Examples are given for the purpose of illustrating the present invention:

EXAMPLE 1

Glutaric acid ω-orthotrimethyl ester-ω'-cyanomethyl ester

Equivalent amounts of the potassium salt of glutaric acid monoorthotrimethyl ester and chloroacetonitrile and a catalytic amount of a crown ether or of a kryptate are mixed in 20 ml. chloroform and the mixture is stirred for 8 days at ambient temperature. Precipitated sodium chloride is filtered off and the filtrate is shaken out with an aqueous solution of sodium bicarbonate, dried and evaporated. The desired cyanomethyl ester remains behind in the form of a colourless oil.

EXAMPLE 2

Glutaric acid ω-orthotrimethyl ester-ω'-hydroxysuccinimide ester

This compound is prepared in a manner analogous to that described in Example 1 but using the methyl-sulphonate or p-toluene-sulphonate of hydroxysuccinimide instead of chloroacetonitrile.

EXAMPLE 3

Digoxin-4'''-glutaryl-cyanomethyl ester

To 2 g. of the glutaric acid ω-orthotrimethyl ester-ω'-cyanomethyl ester prepared according to Example 1 in 20 ml. anhydrous tetrahydrofuran are added 100 mg. p-toluene-sulphonic acid and 1.5 g. digoxin. While stirring, at ambient temperature, the digoxin goes slowly into solution. After 6 hours, the solution is adjusted to pH 2 with 4 ml. 0.1 N hydrochloric acid, then further stirred for half an hour and finally adjusted to pH 6 with 0.1N aqueous sodium hydroxide solution. The solution is then evaporated, the residue is taken up with absolute ethanol and again evaporated. An oil remains behind from which the desired compound slowly crystallises out in the cold. It is recrystallised from ethyl acetate/petroleum ether; m.p. 170–180° C. (decomposition).

Analysis: calculated: C 61.5%; H 7.4%; N 1.5% found: 61.46%; 7.79%; 1.17%.

EXAMPLE 4

Digoxin-4'''-glutaryl-hydroxysuccinimide ester

To 2 g. of the glutaric acid ω-orthotrimethyl ester-ω'-hydroxysuccinimide ester prepared according to Example 2 in 20 ml. anhydrous tetrahydrofuran are added 100 mg. p-toluene-sulphonic acid and 1.5 g. digoxin, the subsequent procedure being as described in Example 3; m.p. 125–140° C. (decomposition).

Analysis: calculated: C 60.5%; H 7.35%; N 1.4% found: 59.89%; 7.51%; 1.24%

The reactions described in the following, by way of Example, illustrate in more detail the advantageous use of the new compounds according to the present invention for the preparation of reagents for the investigation of Digitalis glycosides.

Digoxin-4'''-glutaryl-tyramide 0.5 g. of the active dicarboxylic acid prepared according to Example 3 or 4, 0.082 g. tyramine and 0.082 ml. triethylamine are stirred for 4 days at ambient temperature in 20 ml. anhydrous tetrahydrofuran. The tetrahydrofuran is then stripped off and the residue is taken up in methylene chloride and shaken out twice with 0.1N hydrochloric acid and once with water. The organic phase is dried and evaporated and the residue is taken up in ethyl acetate and precipitated with petroleum ether. The crystalline product so obtained is dissolved in ethyl acetate and chromatographed on a silica gel column. An impurity first runs through, whereafter the pure product is eluted with tetrahydrofuran. The eluate is evaporated and the residue is mixed with ethyl acetate. Upon adding petroleum ether, pure digoxin-4'''-glutaryl-tyramide crystallises out (m.p. 120–160° C. (decomp.)) which, after radioactive marking, is an outstanding reagent for the determination of digoxin in aqueous or physiological solution.

Digoxin-bovine serum albumin conjugate

To a 5% solution of bovine serum albumin in an aqueous potassium carbonate solution (pH 8.5), there is added dropwise an ethanolic solution of an active dicarboxylic acid ester prepared according to Example 3 or 4. After stirring the reaction mixture for several days at ambient temperature, a white precipitate is obtained which is centrifuged off and washed with ethyl acetate. Not only the centrifugate but also the residue, which is dispersed in water, are dialysed for one day against running water. The solution of the residue is then immediately lyophilised. The solution of the centrifugate is adjusted with 0.1N hydrochloric acid to pH 7, evaporated, subsequently taken up in ethanol and adjusted to pH 4.5. A further part of the conjugate thereby precipitates out. This is taken up in 10 ml. 0.15N aqueous sodium bicarbonate solution, dialysed for 3 days against running water and subsequently lyophilised.

In an analogous manner, edestin- and polylysine-digoxin conjugates can be prepared from the active dicarboxylic acid esters prepared according to Example 3 or 4 which conjugates, like the digoxin-bovine serum albumin conjugate, are outstanding immunogens.

A peroxidase-digoxin derivative can also be prepared in a manner analogous to that used for preparing the digoxin-bovine serum albumin conjugate. In this case, the ethanol content of the reaction solution is less than 20% and dialysis is against a 0.1N tris buffer solution (pH 6.2). The peroxidase-digoxin derivative is an outstanding enzyme test reagent for the determination of digoxin. Condensation on to aminohexyl-sepharose can also be carried out analogously.

It will be understood that the specification and examples are illustrative but not limitative of the present invention and that other embodiments within the spirit and scope of the invention will suggest themselves to those skilled in the art.

What is claimed is:

1. Reactive asymmetrical dicarboxylic acid esters of the general formula

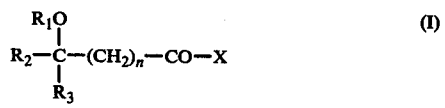

(I)

wherein
$R_1$ is a digoxin or digitoxin residue,
$R_2$ and $R_3$ together represent an oxygen atom,
X is succinimido-N-oxy, and
n is 2,3,4 or 5.

2. Dicarboxylic acid ester compounds as claimed in claim 1 wherein $R_1$ is a digoxin residue.

3. Dicarboxylic acid ester compounds as claimed in claim 1 wherein $R_1$ is a digitoxin residue.

4. Dicarboxylic acid ester compounds as claimed in claim 1 designated digoxin-4'''-glutaryl-hydroxysuccinimide ester.